(12) United States Patent  
Waller

(10) Patent No.: US 8,007,507 B2
(45) Date of Patent: Aug. 30, 2011

(54) INTRAGASTRIC BAG APPARATUS AND METHOD OF DELIVERY FOR TREATING OBESITY

(75) Inventor: David F. Waller, Tampa, FL (US)

(73) Assignee: Cook Medical Technologies LLC, Bloomington, IN (US)

( * ) Notice: Subject to any disclaimer, the term of this patent is extended or adjusted under 35 U.S.C. 154(b) by 1055 days.

(21) Appl. No.: 11/801,442

(22) Filed: May 10, 2007

(65) Prior Publication Data

US 2008/0281257 A1 Nov. 13, 2008

(51) Int. Cl.
A61M 29/00 (2006.01)
(52) U.S. Cl. ..................... 606/191; 623/23.65
(58) Field of Classification Search .......... 606/191–200, 606/113, 114, 127, 128; 623/23.64–38; 604/164.01, 604/164.12, 104–109
See application file for complete search history.

(56) References Cited

U.S. PATENT DOCUMENTS

| | | | |
|---|---|---|---|
| 2,508,690 A | 5/1950 | Schmerl | |
| 4,133,315 A | 1/1979 | Berman et al. | |
| 4,134,405 A | 1/1979 | Smit | |
| 4,246,893 A | 1/1981 | Berson | |
| 4,315,509 A | 2/1982 | Smit | |
| 4,403,604 A | 9/1983 | Wilkinson et al. | |
| 4,416,267 A | 11/1983 | Garren et al. | |
| 4,485,805 A | 12/1984 | Foster, Jr. | |
| 4,558,699 A | 12/1985 | Bashour | |
| 4,607,618 A | 8/1986 | Angelchik | |
| 4,694,827 A | 9/1987 | Weiner et al. | |
| 4,696,288 A | 9/1987 | Kuzmak et al. | |
| 4,723,547 A | 2/1988 | Kullas et al. | |
| 4,803,985 A | 2/1989 | Hill | |
| 4,878,905 A | 11/1989 | Blass | |
| 4,899,747 A | 2/1990 | Garren et al. | |
| 4,925,446 A | 5/1990 | Garay et al. | |
| 4,952,339 A | 8/1990 | Temus et al. | |
| 5,129,915 A | 7/1992 | Cantenys | |
| 5,234,454 A | 8/1993 | Bangs | |
| 5,246,456 A | 9/1993 | Wilkinson | |
| 5,306,300 A | 4/1994 | Berry | |
| 5,327,914 A | 7/1994 | Shlain | |
| 5,345,949 A | 9/1994 | Shlain | |
| 5,868,141 A | 2/1999 | Ellias | |
| 5,938,669 A | 8/1999 | Klaiber et al. | |
| 5,993,473 A | 11/1999 | Chan et al. | |

(Continued)

FOREIGN PATENT DOCUMENTS

EP 0137 878 11/1983

*Primary Examiner* — Gary Jackson
*Assistant Examiner* — Christopher Schubert
(74) *Attorney, Agent, or Firm* — Brinks Hofer Gilson & Lione

(57) ABSTRACT

A delivery system and method of use thereof for introducing an intragastric bag and filler strip into a gastric lumen are described. The delivery system includes a multi-lumen overtube, one or retractable hooks, an endoscopic looping device, and a pusher rod. The intragastric bag is attached and loaded into the overtube. The overtube is then deployed within the gastric lumen. A pusher rod pushes the distal end of the intragastric bag out of the overtube and into the gastric lumen. With the intragastric bag open, the filler strip is advanced into the intragastric bag using the pusher rod. The endoscopic loop is then tightened around the proximal end of the intragastric bag so that the filler strip remains entrapped within the intragastric bag.

4 Claims, 15 Drawing Sheets

U.S. PATENT DOCUMENTS

| | | |
|---|---|---|
| 6,067,991 A | 5/2000 | Forsell |
| 6,210,347 B1 | 4/2001 | Forsell |
| 6,427,089 B1 | 7/2002 | Knowlton |
| 6,450,946 B1 | 9/2002 | Forsell |
| 6,454,699 B1 | 9/2002 | Forsell |
| 6,460,543 B1 | 10/2002 | Forsell |
| 6,511,490 B2 | 1/2003 | Robert |
| 6,540,789 B1 | 4/2003 | Silverman et al. |
| 6,558,400 B2 | 5/2003 | Deem et al. |
| 6,627,206 B2 | 9/2003 | Lloyd |
| 6,656,194 B1 | 12/2003 | Gannoe et al. |
| 6,675,809 B2 | 1/2004 | Stack et al. |
| 6,676,674 B1 | 1/2004 | Dudai |
| 6,733,512 B2 | 5/2004 | McGhan |
| 6,740,121 B2 | 5/2004 | Geitz |
| 6,746,460 B2 | 6/2004 | Gannoe et al. |
| 6,755,869 B2 | 6/2004 | Geitz |
| 6,802,868 B2 | 10/2004 | Silverman et al. |
| 6,845,776 B2 | 1/2005 | Stack et al. |
| 6,879,859 B1 | 4/2005 | Boveja |
| 6,916,326 B2 | 7/2005 | Benchetrit |
| 6,946,002 B2 | 9/2005 | Geitz |
| 6,981,980 B2 | 1/2006 | Sampson et al. |
| 6,994,715 B2 | 2/2006 | Gannoe et al. |
| 7,033,373 B2 * | 4/2006 | de la Torre et al. ............ 606/191 |
| 7,033,384 B2 | 4/2006 | Gannoe et al. |
| 7,037,344 B2 | 5/2006 | Kagan et al. |
| 7,054,690 B2 | 5/2006 | Imran |
| 7,056,305 B2 | 6/2006 | Garza Alvarez |
| 7,066,945 B2 | 6/2006 | Hashiba et al. |
| 7,090,699 B2 | 8/2006 | Geitz |
| 7,097,665 B2 * | 8/2006 | Stack et al. ................. 623/23.65 |
| 7,112,186 B2 | 9/2006 | Shah |
| 7,121,283 B2 | 10/2006 | Stack et al. |
| 7,152,607 B2 | 12/2006 | Stack et al. |
| 7,172,613 B2 | 2/2007 | Wazne |
| 7,175,638 B2 | 2/2007 | Gannoe et al. |
| 7,177,693 B2 | 2/2007 | Starkebaum |
| 2001/0011543 A1 | 8/2001 | Forsell |
| 2002/0188354 A1 | 12/2002 | Peghini |
| 2003/0049325 A1 | 3/2003 | Suwelack et al. |
| 2003/0109892 A1 | 6/2003 | Deem et al. |
| 2003/0120265 A1 | 6/2003 | Deem et al. |
| 2003/0158564 A1 | 8/2003 | Benchetrit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0039452 A1 | 2/2004 | Bessler |
| 2004/0044353 A1 | 3/2004 | Gannoe |
| 2004/0044354 A1 | 3/2004 | Gannoe et al. |
| 2004/0049209 A1 | 3/2004 | Benchetrit |
| 2004/0082963 A1 | 4/2004 | Gannoe et al. |
| 2004/0092892 A1 | 5/2004 | Kagan et al. |
| 2004/0092974 A1 | 5/2004 | Gannoe et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0153106 A1 | 8/2004 | Dudai |
| 2004/0158331 A1 | 8/2004 | Stack et al. |
| 2004/0186503 A1 | 9/2004 | DeLegge |
| 2004/0220682 A1 | 11/2004 | Levine et al. |
| 2004/0243152 A1 | 12/2004 | Taylor et al. |
| 2005/0049718 A1 | 3/2005 | Dann et al. |
| 2005/0096750 A1 | 5/2005 | Kagan et al. |
| 2005/0149141 A1 | 7/2005 | Starkebaum |
| 2005/0149142 A1 | 7/2005 | Starkebaum |
| 2005/0177181 A1 | 8/2005 | Kagan et al. |
| 2005/0192531 A1 | 9/2005 | Birk |
| 2005/0192614 A1 | 9/2005 | Binmoeller |
| 2005/0209653 A1 | 9/2005 | Herbert et al. |
| 2005/0222637 A1 | 10/2005 | Chen |
| 2005/0222638 A1 | 10/2005 | Foley et al. |
| 2005/0240239 A1 | 10/2005 | Bojeva et al. |
| 2005/0240279 A1 | 10/2005 | Kagan et al. |
| 2005/0245957 A1 | 11/2005 | Starkebaum et al. |
| 2005/0246037 A1 | 11/2005 | Starkebaum |
| 2005/0250979 A1 | 11/2005 | Coe |
| 2005/0256587 A1 | 11/2005 | Egan |
| 2005/0267405 A1 | 12/2005 | Shah |
| 2006/0015125 A1 * | 1/2006 | Swain ........................ 606/151 |
| 2006/0015151 A1 | 1/2006 | Aldrich |
| 2006/0020247 A1 | 1/2006 | Kagan et al. |
| 2006/0030949 A1 | 2/2006 | Geitz |
| 2006/0074450 A1 | 4/2006 | Boveja et al. |
| 2006/0079944 A1 | 4/2006 | Imran |
| 2006/0089571 A1 | 4/2006 | Gertner |
| 2006/0129027 A1 | 6/2006 | Catona |
| 2006/0129094 A1 | 6/2006 | Shah |
| 2006/0161172 A1 | 7/2006 | Levine et al. |
| 2006/0178722 A1 * | 8/2006 | Jaker et al. ................... 623/1.11 |
| 2006/0206063 A1 | 9/2006 | Kagan et al. |
| 2006/0206064 A1 | 9/2006 | Kagan et al. |
| 2006/0206160 A1 | 9/2006 | Cigaina et al. |
| 2006/0249165 A1 | 11/2006 | Silverman et al. |
| 2006/0253142 A1 | 11/2006 | Bjerken |
| 2006/0257444 A1 | 11/2006 | Tropsha et al. |
| 2006/0257445 A1 | 11/2006 | Tropsha et al. |
| 2006/0257446 A1 | 11/2006 | Tropsha et al. |
| 2006/0282107 A1 | 12/2006 | Hashiba et al. |
| 2006/0293742 A1 | 12/2006 | Dann et al. |
| 2007/0004963 A1 | 1/2007 | Benchetrit |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0038308 A1 | 2/2007 | Geitz |

\* cited by examiner

INTRAGASTRIC BAG APPARATUS AND METHOD OF DELIVERY FOR TREATING OBESITY

TECHNICAL FIELD

This invention relates to medical devices, and more particularly to obesity treatment devices that can be placed in the stomach of a patient to reduce the size of the stomach reservoir or to place pressure on the inside surface of the stomach.

BACKGROUND OF THE INVENTION

It is well known that obesity is a very difficult condition to treat. Methods of treatment are varied, and include drugs, behavior therapy, and physical exercise, or often a combinational approach involving two or more of these methods. Unfortunately, results are seldom long term, with many patients eventually returning to their original weight over time. For that reason, obesity, particularly morbid obesity, is often considered an incurable condition. More invasive approaches have been available which have yielded good results in many patients. These include surgical options such as bypass operations or gastroplasty. However, these procedures carry high risks and are therefore not appropriate for most patients.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These balloons are typically cylindrical or pear-shaped, generally range in size from 200-500 ml or more, are made of an elastomer such as silicone, polyurethane, or latex, and are filled with air, water, or saline. While some studies demonstrated modest weight loss, the effects of these balloons often diminished after three or four weeks, possibly due to the gradual distension of the stomach or the fact that the body adjusted to the presence of the balloon. Other balloons include a tube exiting the nasal passage that allows the balloon to be periodically deflated and re-insufflated to better simulate normal food intake. However, the disadvantages of having an inflation tube exiting the nose are obvious.

The experience with balloons as a method of treating obesity has provided uncertain results, and has been frequently disappointing. Some trials failed to show significant weight loss over a placebo, or were ineffective unless the balloon placement procedure was combined with a low-calorie diet. Complications have also been observed, such as gastric ulcers, especially with use of fluid-filled balloons, and small bowel obstructions caused by deflated balloons. In addition, there have been documented instances of the balloon blocking off or lodging in the opening to the duodenum, wherein the balloon may act like a ball valve to prevent the stomach contents from emptying into the intestines.

Unrelated to the above-discussed methods for treating obesity, it has been observed that the ingestion of certain indigestible matter, such as fibers, hair, fuzzy materials, etc., can collect in the stomach over time, and eventually form a mass called a bezoar. In some patients, particularly children and the mentally handicapped, bezoars often result from the ingestion of plastic or synthetic materials. In many cases, bezoars can cause indigestion, stomach upset, or vomiting, especially if allowed to grow sufficiently large. It has also been documented that certain individuals having bezoars are subject to weight loss, presumably due to the decrease in the size of the stomach reservoir. Although bezoars may be removed endoscopically, especially in conjunction with a device known as a bezotome or bezotriptor, they, particularly larger ones, often require surgery.

What is needed is an intragastric device that provides the potential weight loss benefits of a bezoar or intragastric balloon without the associated complications. Ideally, such a device should be well-tolerated by the patient, effective over a long period of time, sizable for individual anatomies, and easy to place and retrieve.

SUMMARY OF THE INVENTION

The foregoing problems are solved and a technical advance is achieved by an illustrative obesity treatment apparatus comprising at least one intragastric bag made of a digestive-resistant or substantially indigestible material that is introduced into the gastric lumen of a mammal in a first configuration. The intragastric bag is delivered into the gastric lumen in a partially compacted first configuration, whereby it is then manipulated into, or allowed to assume, a second expanded configuration sufficiently large to reduce the digestion rate of food within the stomach during normal activities and not be passed through the pylorus and into the intestines. Another advance is that the present invention can be effective at a smaller volume within the stomach than existing intragastric devices, such as balloons.

In one aspect of the invention, a delivery system for introducing an intragastric bag and filler strip into a gastric lumen is provided. The delivery system comprises an overtube including a proximal end, a distal end, and a plurality of lumens. The delivery system also includes one or more retractable hooks. Each of the one or more retractable hooks extends through one of the plurality of lumens of the overtube. An endoscopic looping device extends through one of the plurality of lumens of the overtube. The endoscopic looping device is adapted to close an end of the intragastric bag. A pusher rod having a proximal end and a distal end is also provided. The pusher rod is adapted for pushing the intragastric bag into the gastric lumen, and further adapted for pushing the filler strip into the intragastric bag.

In another aspect of the invention, a method for introducing an intragastric bag into a gastric lumen is provided. A delivery system is provided that comprises an overtube including a proximal end, a distal end, and a plurality of lumens. The delivery system also includes one or more retractable hooks. Each of the one or more retractable hooks extends through one of the plurality of lumens of the overtube. An endoscopic looping device extends through one of the plurality of lumens of the overtube. The endoscopic looping device is adapted to close an end of the intragastric bag. A pusher rod having a proximal end and a distal end is also provided. The pusher rod is adapted for pushing the intragastric bag into the gastric lumen, and further adapted for pushing the filler strip into the intragastric bag. The one or more retractable hooks within the plurality of lumens are positioned such that the one or more retractable hooks extend from the distal end of the overtube to attain a curved configuration. The intragastric bag is loaded into the main lumen of the overtube, the intragastric bag having a first compressed configuration within the main lumen, wherein the proximal end of the intragastric bag secures to the distal end of the overtube by securing the proximal end of the bag to the one or more retractable hooks. The overtube is positioned within the gastric lumen such that the distal end of the overtube is positioned at a target site within the gastric lumen.

In another aspect of the invention, a method for introducing an intragastric bag and filler strip into a gastric lumen is provided. A delivery system is provided comprising an overtube including a proximal end, a distal end, a main lumen, and a plurality of lumens smaller than the main lumen. One or more retractable hooks extend through the plurality of lumens. An endoscopic looping device is affixed to one of the plurality of lumens. The endoscopic looping device is adapted to cinch a proximal end of the intragastric bag. A pusher rod has a proximal end and a distal end. The pusher rod includes flaps at the distal end. The flaps are adapted for pushing the intragastric bag into the gastric lumen and pushing the filler strip into the intragastric bag. The intragastric bag is loaded into the main lumen of the overtube. The intragastric bag has a first compressed configuration within the main lumen. The proximal end of the intragastric bag secures to the distal end of the overtube by anchoring to the curved configuration of the one or more retractable hooks. The overtube is positioned within the gastric lumen such that the distal end of the overtube having the intragastric bag attached thereto is positioned at a target site within the gastric lumen. A distal end of the intragastric bag is pushed with the pusher rod until the distal end of the intragastric bag passes beyond the distal end of the overtube and is delivered into the gastric lumen. The filler strip is advanced distally along the main lumen of the overtube.

These and other advantages, as well as the invention itself, will become apparent in the details of construction and operation as more fully described below. Moreover, it should be appreciated that several aspects of the invention can be used with other types of intragastric devices or procedures used for the treatment of obesity.

BRIEF DESCRIPTION OF SEVERAL VIEWS OF THE DRAWINGS

Several embodiments of the present invention will now be described by way of example with reference to the accompanying drawings, in which.

DETAILED DESCRIPTION OF THE INVENTION

The obesity treatment apparatus of the present invention depicted in FIGS. 1-17 comprises at least one intragastric bag 11 comprising a digestive-resistant or indigestible material 12 sized and configured such that the intragastric bag 11 can be delivered into the stomach of a mammalian patient and reside therein, and reduce the overall rate of digestion of the patient. As used herein, the terms digestive-resistant and indigestible are intended to mean that the material used is not subject to the degrative effects of stomach acid and enzymes, or the general environment found within the gastric system over an extended period of time, therefore allowing the device to remain intact for the intended life of the device. However, this does not necessarily mean that the material cannot be degraded over time. One skilled in medical arts and gastrological devices would readily appreciate the range of materials that would be suitable for use as a long-term intragastric bag.

The intragastric bag 11 may comprise a digestive-resistant or indigestible material 12. For example, many well-known plastics have suitable properties, including selected polyesters, polyurethanes, polyethylenes, polyamides, silicone, or other possible materials. Mammalian hair has been found to form natural bezoars, and thus, is also a possible material. However, some materials, such as certain polyamides, have been found to expand over time, which can be an undesirable property. Most other natural materials are generally much less resistant to acids and enzymes, and would therefore typically require treatment or combination with resistant materials to function long term, unless a shorter-term placement is intended or desired.

Figure 1:
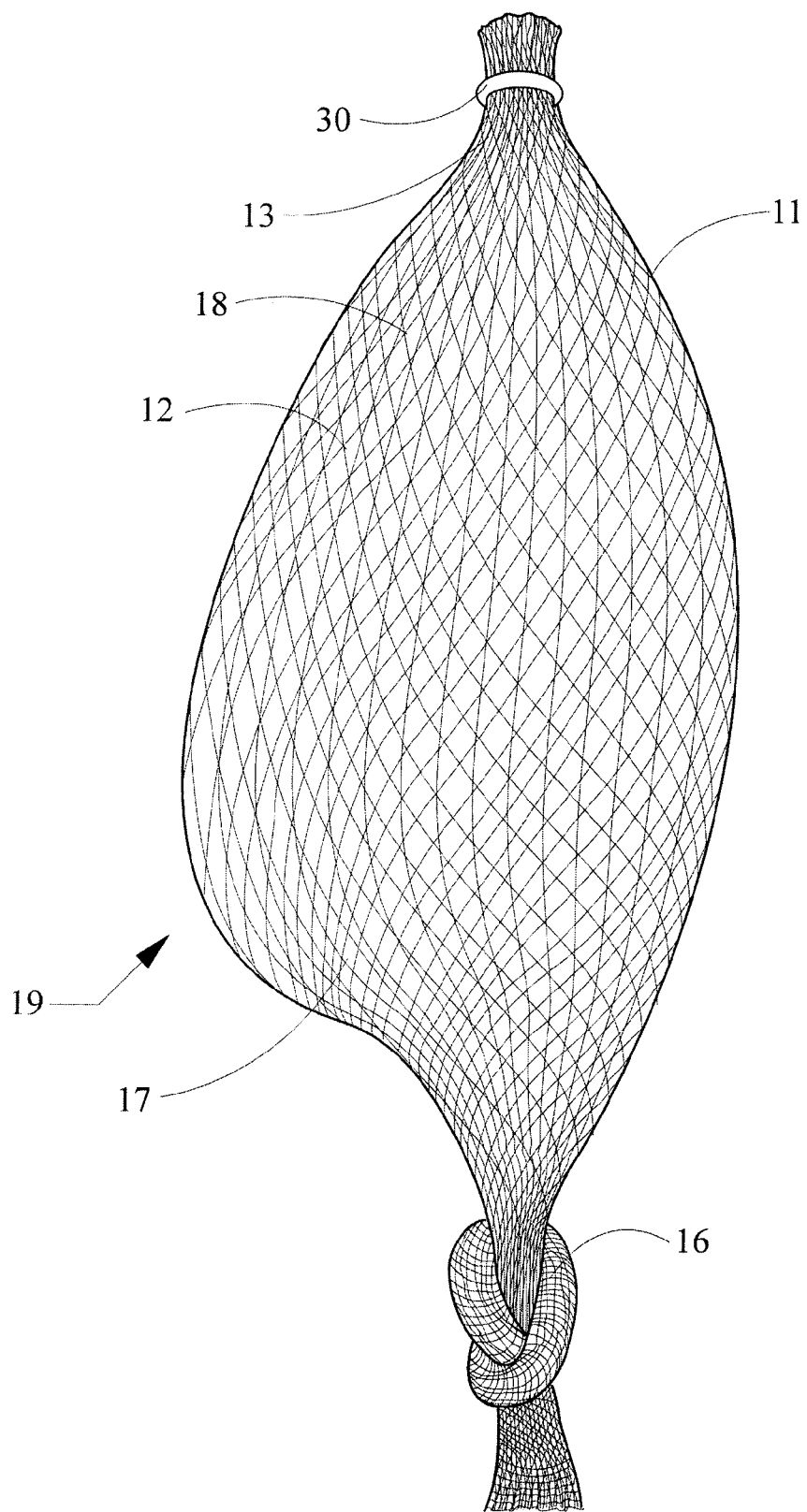
FIG. 1 depicts a pictorial view of an intragastric bag of the present invention.

FIG. 1 depicts a single intragastric bag 11 in which the intragastric bag 11 comprises a preformed expandable digestive-resistant material 12. In this embodiment, the intragastric bag 11 comprises a mesh material. The intragastric bag 11 may be spherical shaped and includes a proximal end 13, a distal end 14 and a main body 15. The bag 11 may be a tube of mesh material that is tied at one end. The main body 15 provides a plurality of openings 18 configured to receive and entrap food material passing through the gastric lumen of the patient. One of ordinary skill in the art would also appreciate that the size of the intragastric bag 11 is related to the length, width, and material comprising the intragastric bag 11.

The intragastric bag 11 comprises at least one stopper 16 engaged to at least one of the proximal end 13 and distal end 14 of the intragastric bag 11. In this embodiment, the stopper 16 may be formed along the distal end 14 of the intragastric bag 11 by tying a knot utilizing the material 12 of the intragastric bag 11. The stopper 16 at the distal end 14 seals the bag 11. The proximal end 13 of the bag 11 is not sealed with a stopper 16. Rather, the proximal end 13 remains open such that an open bag structure is formed into which a filler material may be inserted, as will be discussed below.

The intragastric bag 11 may comprise varying shapes and configurations to alter or increase the amount of volume or space of the stomach reservoir occupied by the corresponding intragastric bag. Particularly, varying shapes can be selected to provide a feeling of fullness upon engaging the lumen of the patient, i.e., the stomach walls of the patient. Additionally, the intragastric bag 11 can be composed of an expandable material, a low density polyethylene or other suitable material. Likewise, the intragastric bag 11 can comprise varying shapes depending on the particular use or treatment protocol. For example, the shape of the intragastric bags 11 can be selected from the group consisting of circular, round, elliptical, square, triangular, rectangular, pentagonal, and hexagonal or any other suitable three dimensional shapes.

Referring to FIG. 1, the intragastric bag 11 comprises a plurality of openings 18 positioned along the main body 15 of the intragastric bag 11. The plurality of openings 18 reduces the overall mass of the intragastric bag 11 and also decreases the total thickness of the intragastric bag 11 for delivery into the gastric lumen. As best seen in FIG. 1, the intragastric bag 11 is formed from a sheet of relatively biocompatible material having a mesh-like design of varying shapes and dimensions. When positioned within the gastric lumen, the plurality of openings 18 along the main body 15 of the intragastric bag 11 allow gastric fluid to pass through the openings 18 but may entrap other material, such as food particles. Thus, the openings 18 of the intragastric bag 11 provide a filtering effect within the gastric lumen, thus reducing the rate of food digestion of the patient. The entrapping of food particles in the intragastric bag 11 further enhances the expansion of the intragastric bag 11 from a first compressed, delivery configuration 17 (see FIG. 2) to a second expanded configuration 19 (see FIG. 1) that provides an extended feeling of fullness. A variety of sizes for the openings 18 may be utilized. The openings 18 of the intragastric bag 11 should be sized to prevent objects such as the filler strip 100 (discussed below) from falling out of the intragastric bag 11. Accordingly, the mesh openings of the intragastric bag 11 may range from about 1 mm to about 5 mm.

Figure 8:
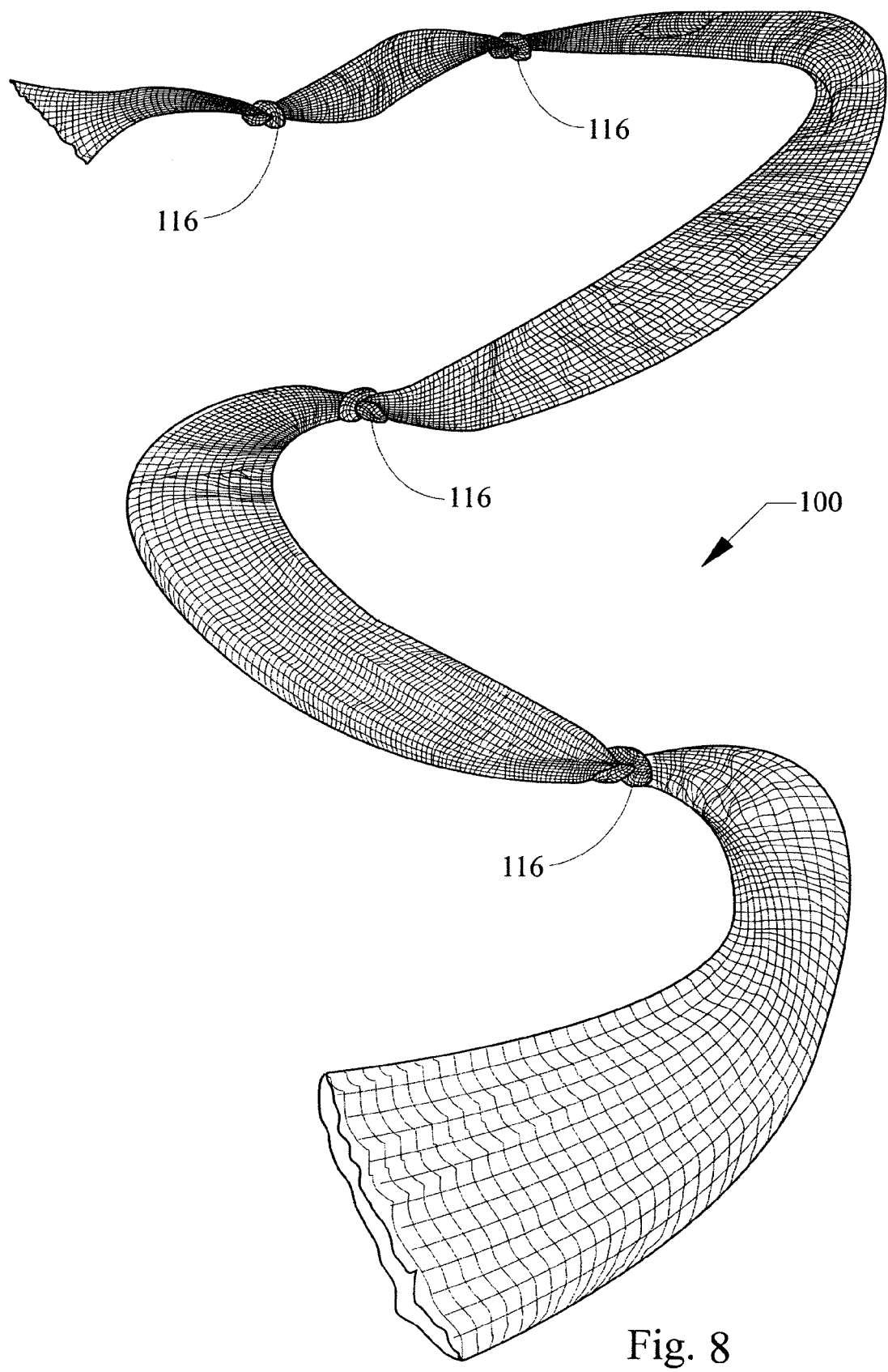
FIG. 8 depicts a pictorial view of another embodiment of an intragastric bag of the present invention.
Figure 10:
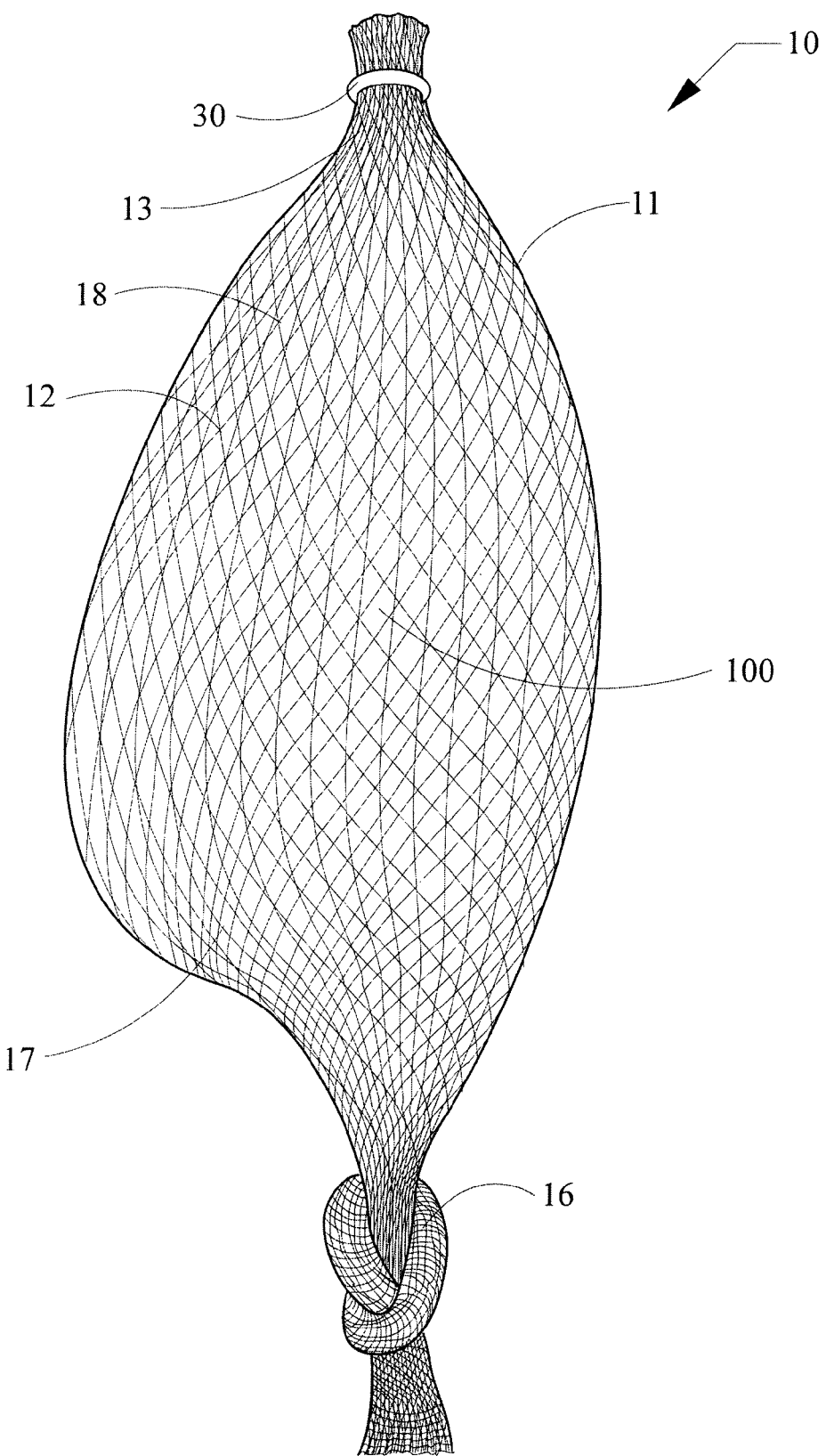
FIG. 10 depicts a pictorial view of the intragastric bag of FIG. 8 upon complete delivery into the gastric lumen.

FIG. 8 shows a filler strip 100 which is inserted into the intragastric bag 11 of FIG. 1 to form the filled bag structure 10 of FIG. 10. Alternatively, the filler strip 100 may be formed from the same mesh material as the intragastric bag 11. The filler strip 100 may be a solid strip of material, as shown in FIG. 8. Insertion of the filler strip 100 into the intragastric bag 11 may provide two functions. First, the filler strip 100 may act as a space filler that fills the bag 11. Second, the filler may help to trap larger food particles to slow digestion. Still referring to FIG. 8, the filler strip 100 also includes knots 116 tied at predetermined distances. The knots 116 may help the pusher rod 1100 (FIGS. 11*a*, 11*b*) to deploy the filler strip 100 into the intragastric bag 11, as will be discussed in greater detail below.

The components of a delivery system for introducing the intragastric bag 11 into a gastric lumen will now be described. The delivery system comprises a multi-lumen overtube 40, retractable hooks 47, a pusher rod 1100 (FIGS. 11*a*, 11*b*, 12), and an endoscopic looping device 30.

Figure 7:
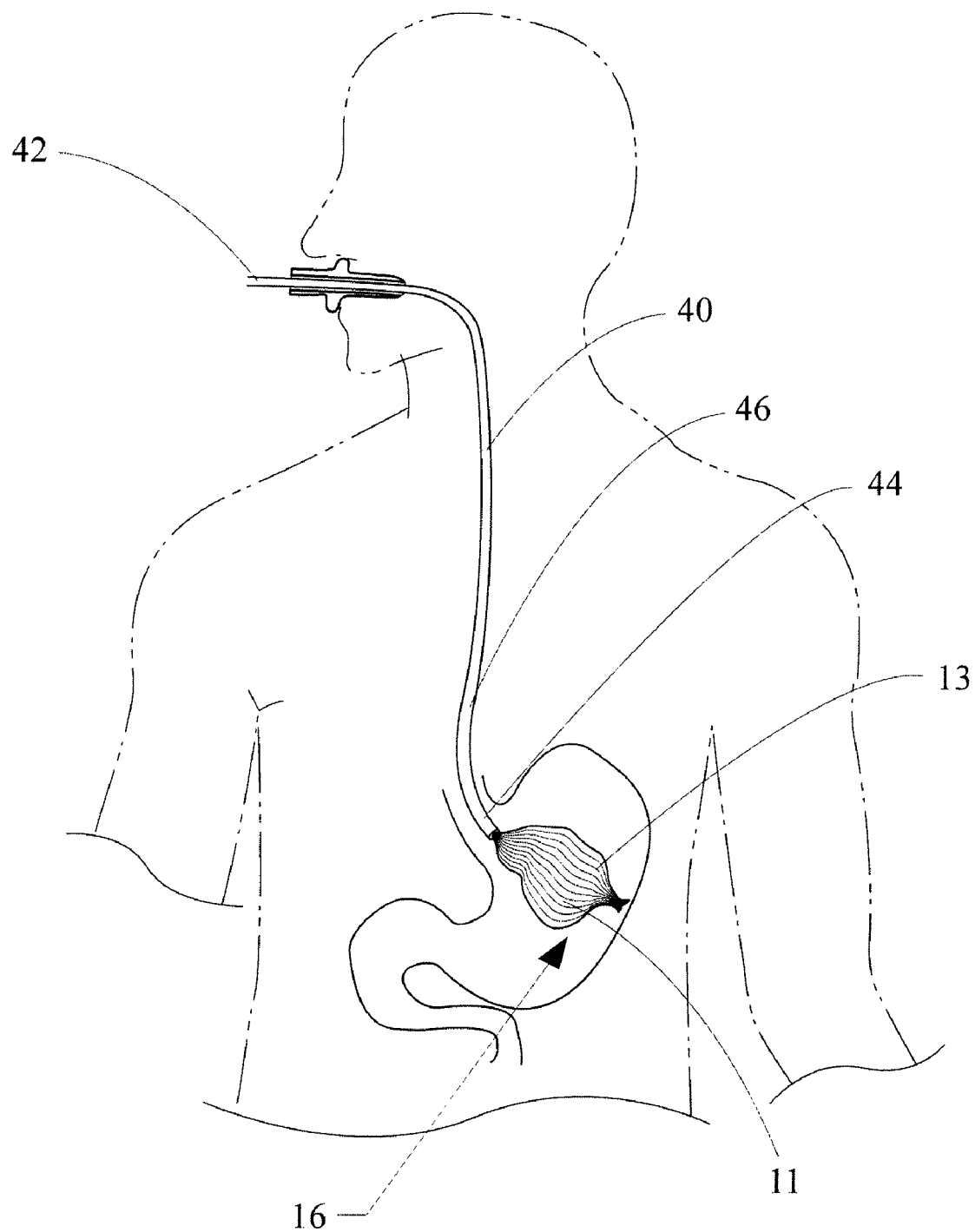
FIG. 7 depicts a partial, cross-sectional view showing an overtube positioned in the mouth and along the esophagus of a patient such that the overtube distal end is positioned within the gastric lumen of the stomach.

The overtube 40 is depicted in FIG. 7. Generally speaking, the overtube 40 serves as a passageway for various devices to pass therethrough. The overtube 40 may be used to deliver the intragastric bag 11 and may be used in combination with an endoscope to establish a passageway to a target delivery site in the stomach. The overtube 40 comprises a proximal end 42, a distal end 44 and a main lumen 45 through which the intragastric bag 11, filler strip 100, and endoscope may pass. The size of the main lumen 45 is related to the size of either the intragastric bag 11 or the endoscope, whichever is larger.

The overtube 40 may have a single-piece construction as shown in the embodiment depicted in FIG. 7. Alternatively, several tubes may be bonded together to form the flexible overtube 40. The overtube 40 may be made from any suitable material known in the art including, but not limited to, polyethylene ether ketone (PEEK), polytetrafluoroethylene (PTFE), polyamide, polyurethane, polyethylene and nylon, including multi-layer or single layer structures and may also include reinforcement wires, braid wires, coils and or filaments.

Figure 3:
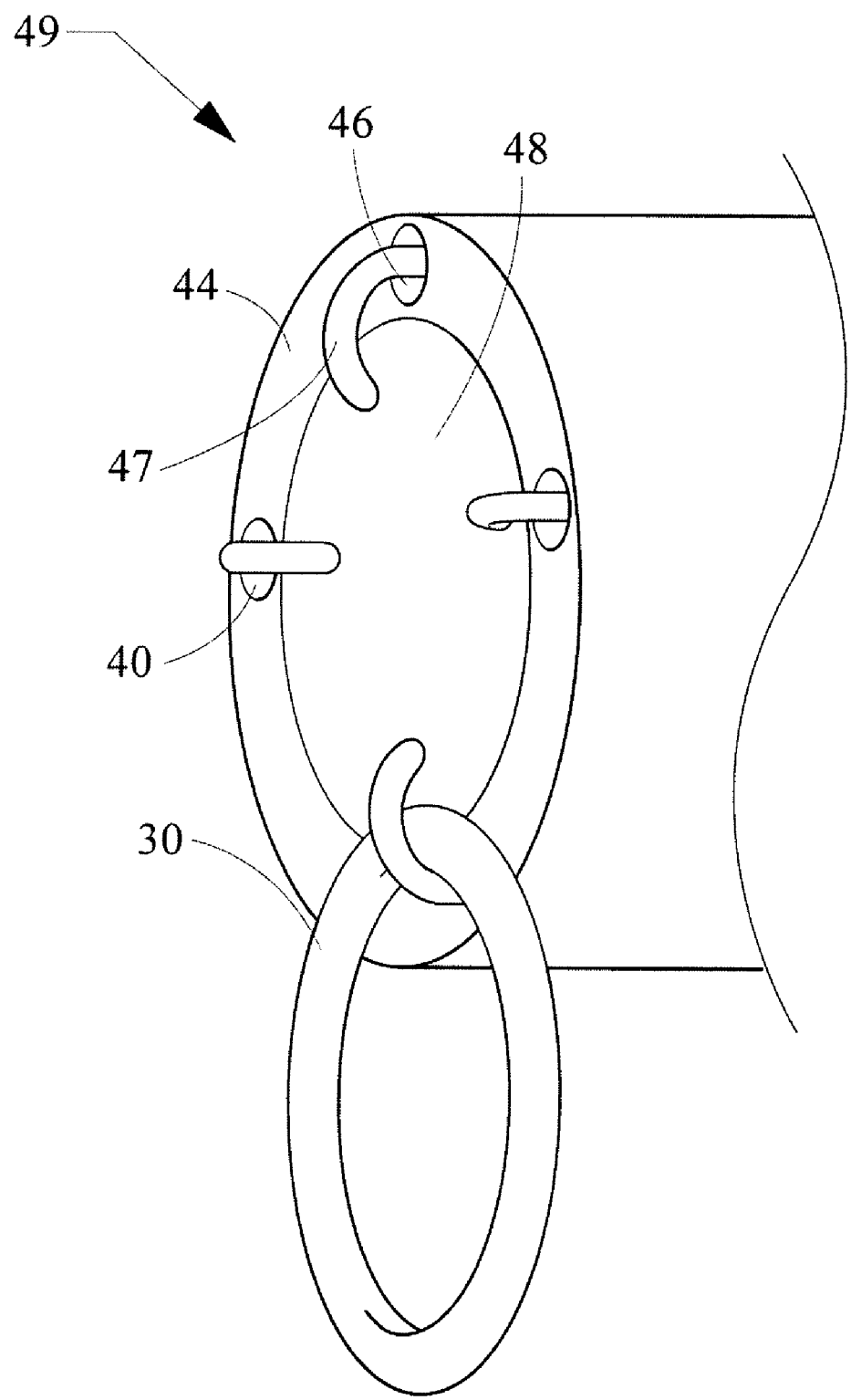
FIG. 3 depicts an end view of the distal end of the delivery tube of FIG. 2 wherein the delivery tube comprises a plurality of retaining elements disposed within a plurality of lumens of the delivery tube.
Figure 4:
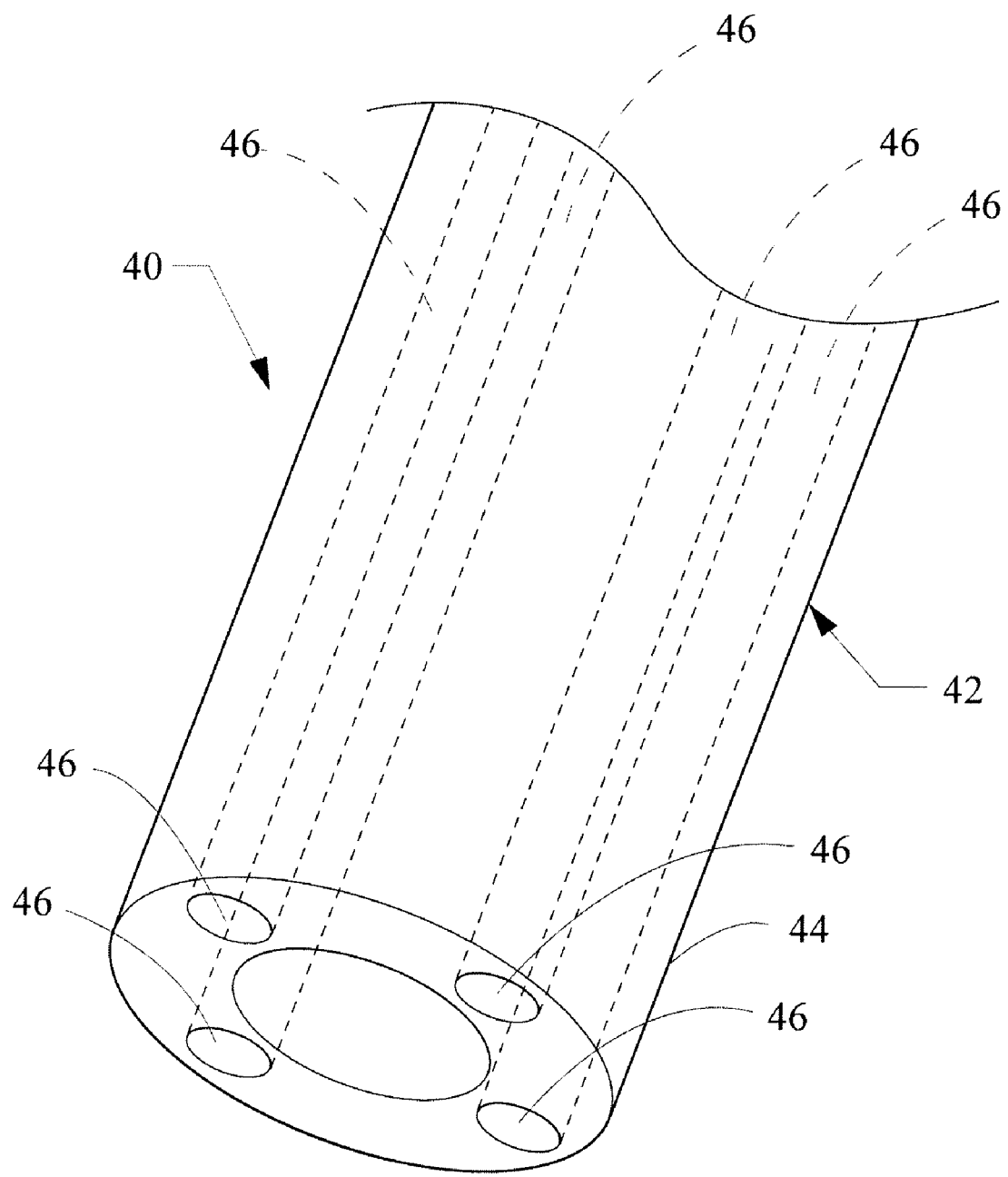
FIG. 4 depicts a pictorial view of the distal end of the delivery tube of the present invention comprising a plurality of lumens.

FIGS. 3 and 4 illustrate the distal end 44 of the overtube 40 of FIG. 7 in greater detail. Referring to FIG. 3, which illustrates an end view of the overtube 40, the overtube 40 is shown to have multiple lumens 46 which are smaller than the main lumen 45. Retractable hooks 47 are shown extending through three upper lumens 46 and an endoscopic loop 30 is shown extending though the lower lumen 46. FIG. 4 shows a perspective view of the distal end 44 of the overtube 40. FIG. 4 shows that each lumen 46 extends between the proximal end 42 and the distal end 44 of the overtube 40 such that lumen 46 is designed to secure the retractable hooks 47 along the length of the overtube.

Figure 2:
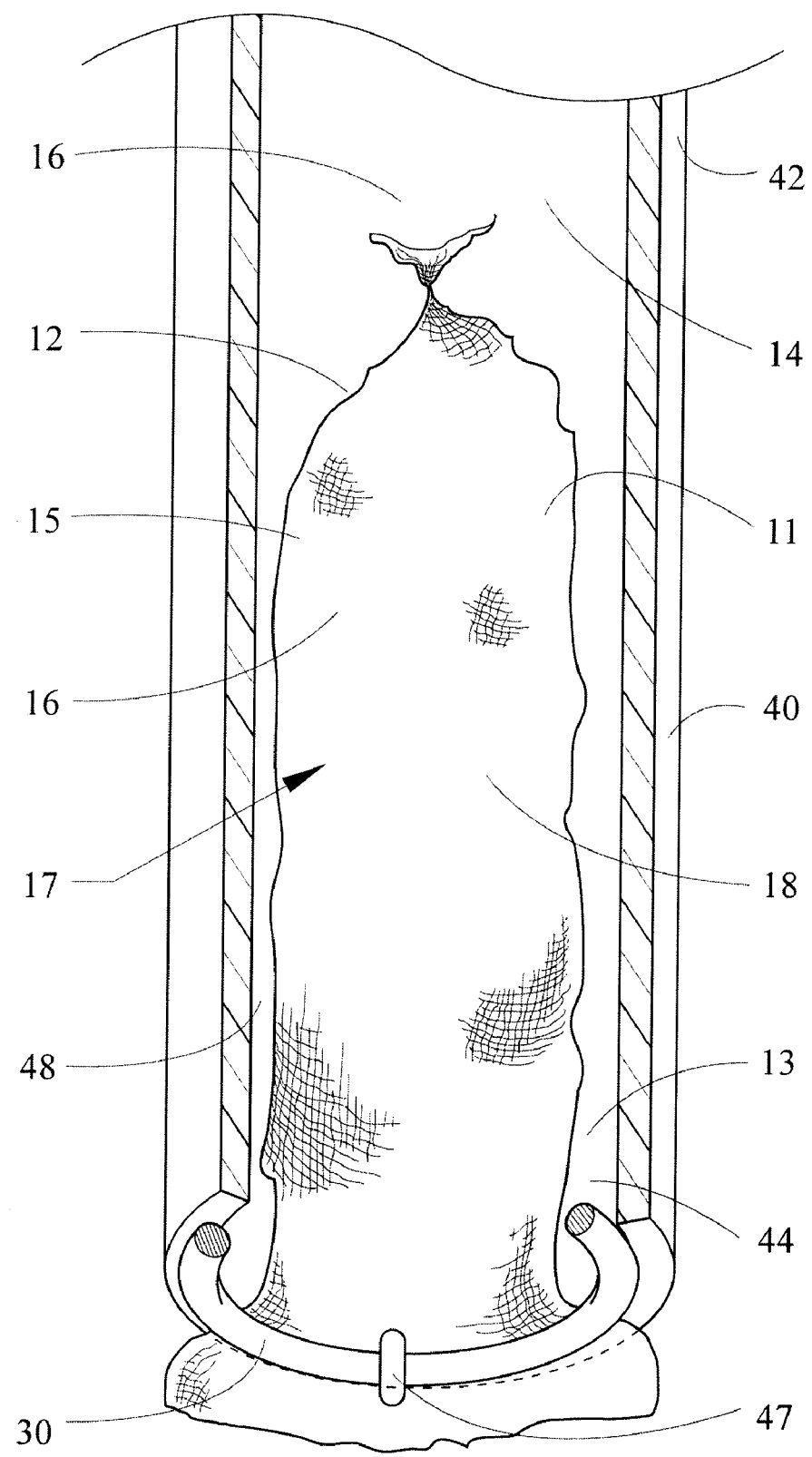
FIG. 2 depicts a pictorial view of the intragastric bag of FIG. 1 loaded onto a delivery tube for insertion into the gastric lumen.
Figure 9:
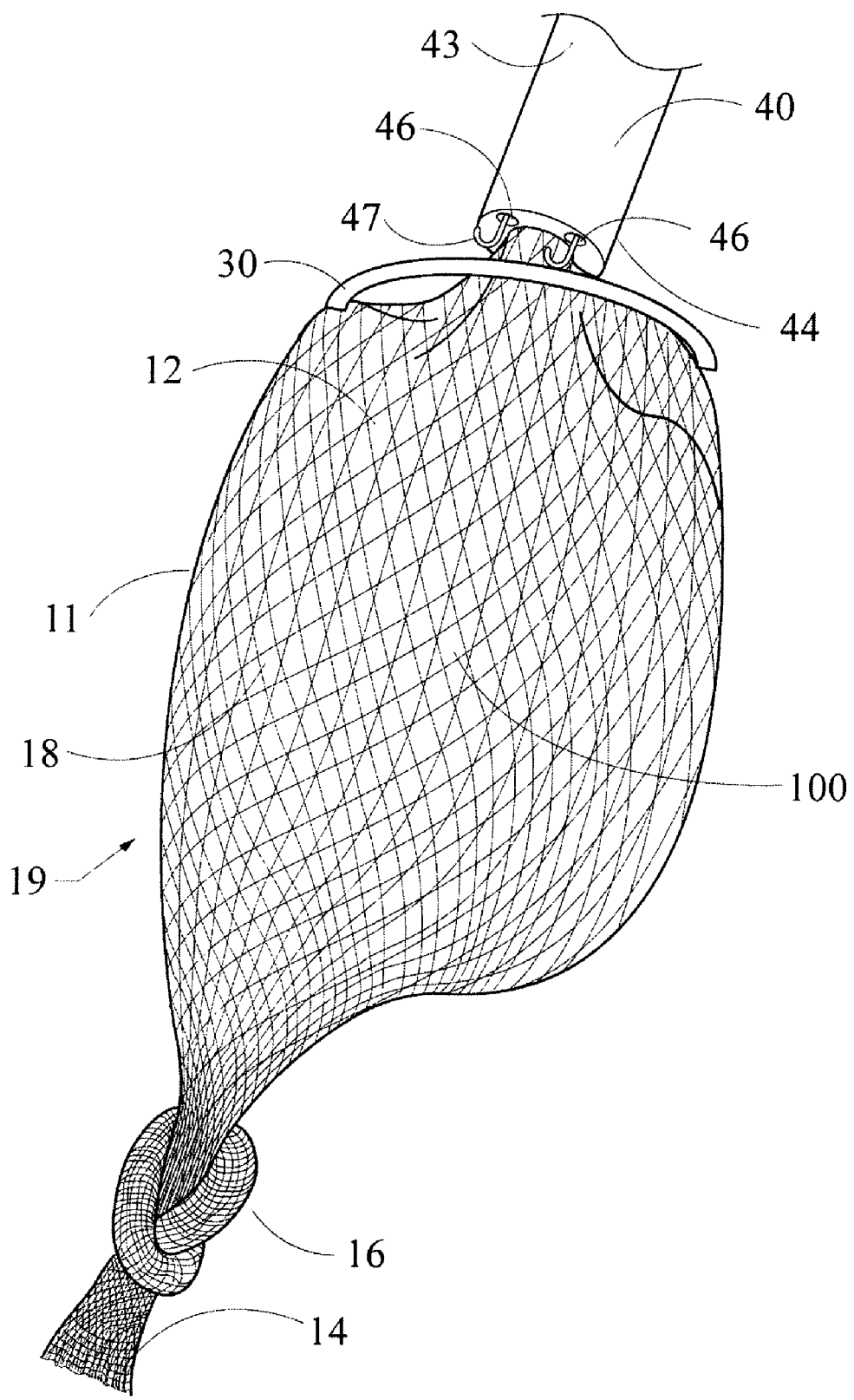
FIG. 9 depicts a pictorial view of the intragastric bag of FIG. 8 during delivery into the main body of the first intragastric bag of FIG. 1 of the present invention.
Figure 12:
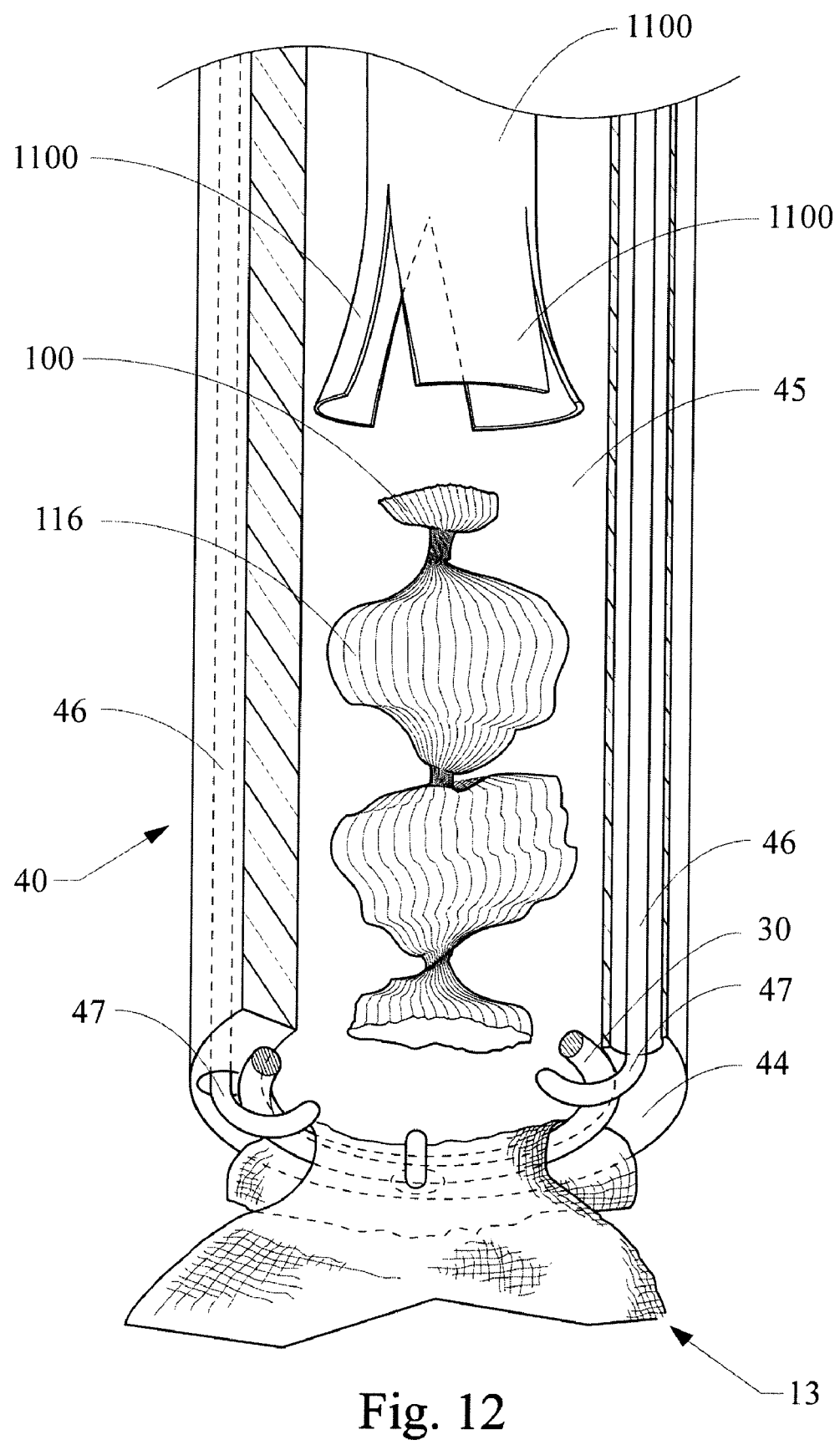
FIG. 12 is a side view of the pusher rod pushing a filler strip distally along a lumen of the overtube.

The retractable hooks 47 are another component of the delivery system for introducing the intragastric bag 11 and filler strip 100 into the gastric lumen. FIG. 2 shows that the retractable hooks 47 secure the proximal end 13 of the intragastric bag 11 to the distal end 44 of the overtube 40, thus providing maneuverability of the intragastric bag 11 during delivery to a target site of the gastric lumen. The retractable hooks 47 also maintain the proximal end 13 of the bag 11 open to allow the filler strip 100 to be inserted into the bag 11, as shown in FIG. 9. FIG. 12 shows the retractable hooks 47 extending through the lumens 46. The retractable hooks 47 are disposed through the lumens 46 and about the perimeter of the overtube 40. Referring to FIG. 4, the retractable hooks 47 are inserted into a proximal end of each lumen 46 of the overtube 40 and extend to the distal end 44 of the overtube 40. As shown in FIG. 3, the retractable hooks 47 are shown curved as they emerge from the distal portion of the lumens 46. This curved shape provides a hook to anchor and secure the bag 11. When the hooks 47 are retracted into their respective lumens 46, the hooks 47 are straightened by the walls of the lumens 46 so as to slip off from the bag 11, thus releasing the proximal end 13 of the bag 11 into the gastric lumen.

Preferably, the hooks 47 are formed from a shape memory alloy utilizing superelastic properties, such as nickel-titanium alloys. By virtue of the superelastic properties of such alloys, the hooks 47 tend to naturally revert to the curved shape when the restraining stress is removed (i.e., when the hooks are advanced past the distal end of each of their respective lumens 46). Accordingly, the stress introduced into the hooks 47 may be released by distally moving a portion of the hooks 47 out of each of their respective lumen 46. Thus, the superelastic properties enable the hooks 47 to move from a substantially straight configuration (when contained within the lumen 46) to a curved configuration (when emerging from the distal end of the lumen 46). Other suitable retractable securing elements may also be used to couple the intragastric bag 11 to the overtube 40 during delivery.

Figure 6:
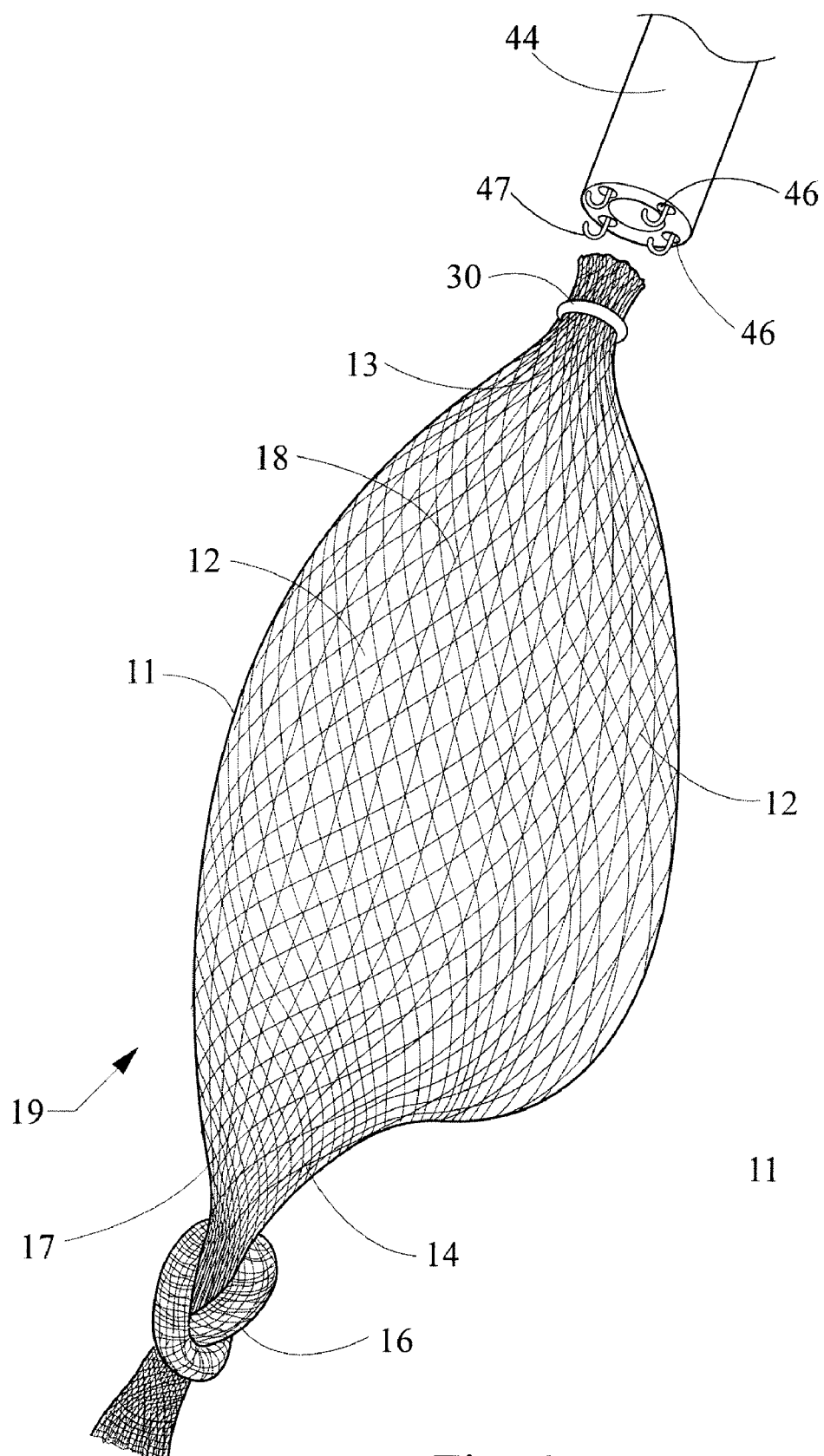
FIG. 6 depicts a pictorial view of the intragastric bag of FIG. 5 of the present invention upon release from the delivery tube into the gastric lumen.
Figure 15:
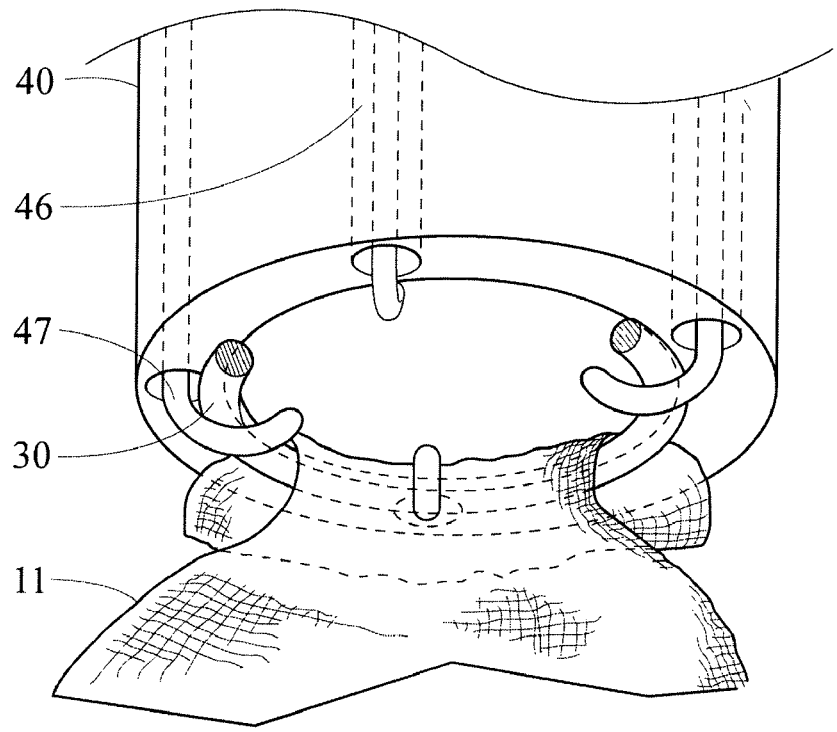
FIG. 15 depicts a pictorial view of the distal end of the intragastric bag disposed beyond the distal end of the delivery tube and anchored by hooks to the distal end of the delivery tube.

The endoscopic looping device 30 is another component of the delivery system for introducing the intragastric bag 11 and filler strip 100 into the gastric lumen. The looping device 30 extends through one of the smaller lumens 46 of the overtube 40, as shown in FIG. 3. The looping device 30 may be a plastic snare that closes about the proximal end 13 of the intragastric bag 11, as shown in FIG. 6 after the filler strip 100 has been inserted therewithin. FIG. 15 shows the looping device 30 positioned about the hooks 47 such that the looping device 30 encircles the bag 11. Positioning of the looping device 30 about the outer surface of each of the hooks 47 enables the looping device 30 to remain rigid when closing the bag 11. Closing of the proximal end 13 of the bag 11 creates an enclosed bag 11 from which the filler strip 100 cannot fall out. The proximal portion of the looping device 30 that extends through a lumen of a delivery tube may be cut or broken off from the distal portion of the looping device which closes the proximal end 13 of the bag 11.

Figure 16:
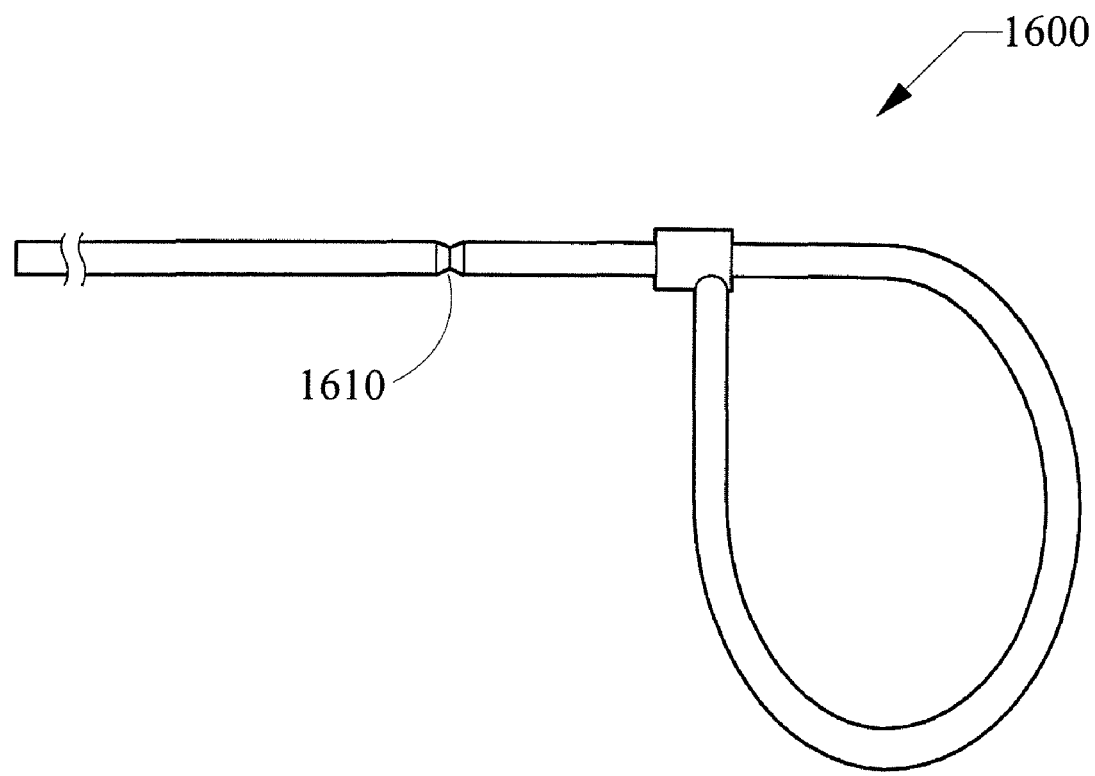
FIGS. 16 and 17 show an alternative endoscopic looping device.
Figure 17:
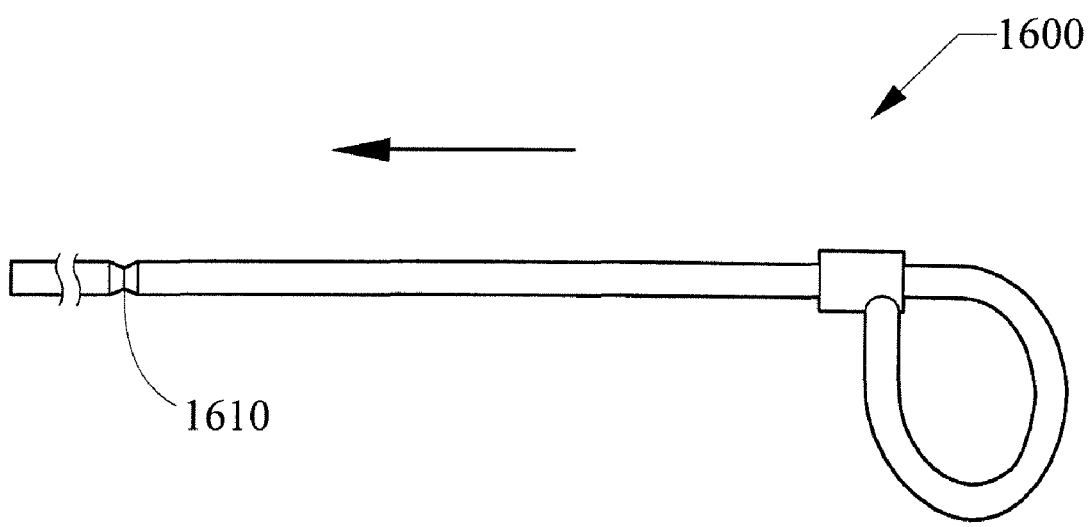

Alternatively, the looping device 30 may comprise a cable tie 1600 as shown in FIGS. 16 and 17. The distal end of the cable tie 1600 forms a loop around the bag 11. The distal end of the cable tie 1600 may be configured about the outer surface of each of the hooks 47. When an end of the bag 11 is ready to be closed, the cable tie 1600 may be pulled so as to reduce the size of the loop about the bag 11 such that bag 11 becomes sealed. FIG. 17 shows that the cable tie 1600 has a weakened region 1610. Further pulling of the cable tie 1600 allows the cable tie 1600 to break off at the weakened region 1610 and allow subsequent removal of the proximal portion of the cable tie 1600.

Figure 11A:
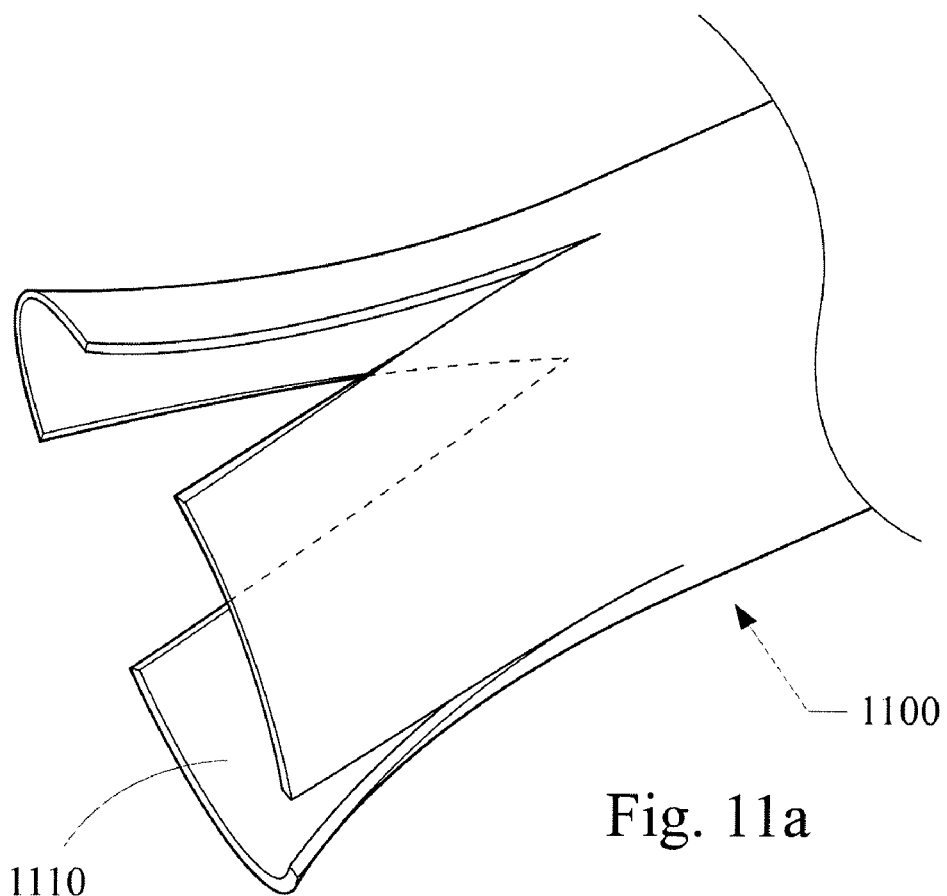
FIG. 11*a* is a side view of a pusher rod.
Figure 11B:
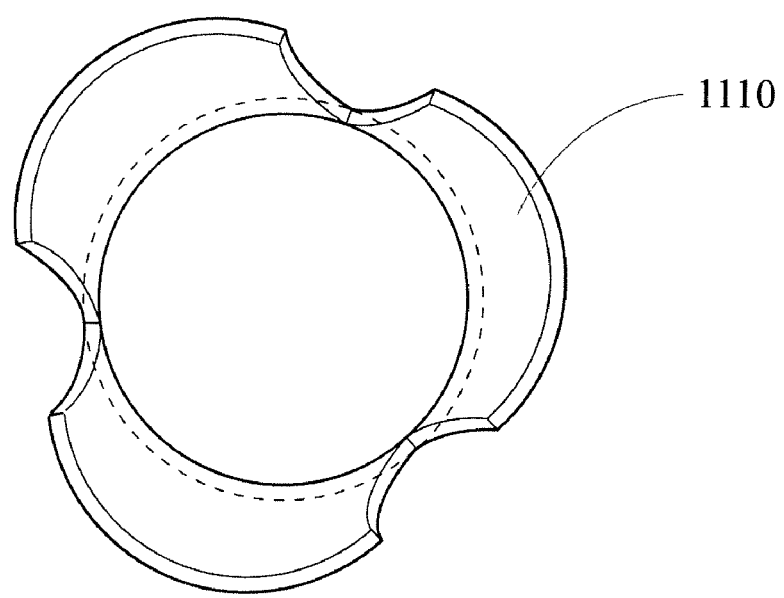
FIG. 11*b* is an end view of the pusher rod of FIG. 11*a*.

FIGS. 11a and 11b show a pusher rod 1100, which is another component of the delivery system for introducing the intragastric bag 11 and filler strip 100 into the gastric lumen. The pusher rod 1100 is used to push the intragastric bag 11 out of the lumen 45 (FIG. 2) of the delivery tube and into the gastric lumen. After the intragastric bag 11 has been deployed, the pusher rod 1100 acts to push the filler strip 100 through the main lumen 45 and into the intragastric bag 11. The pusher rod 1100 contains multiple flaps 1110 for engaging the filler strip 100 as will be discussed below.

Figure 13:
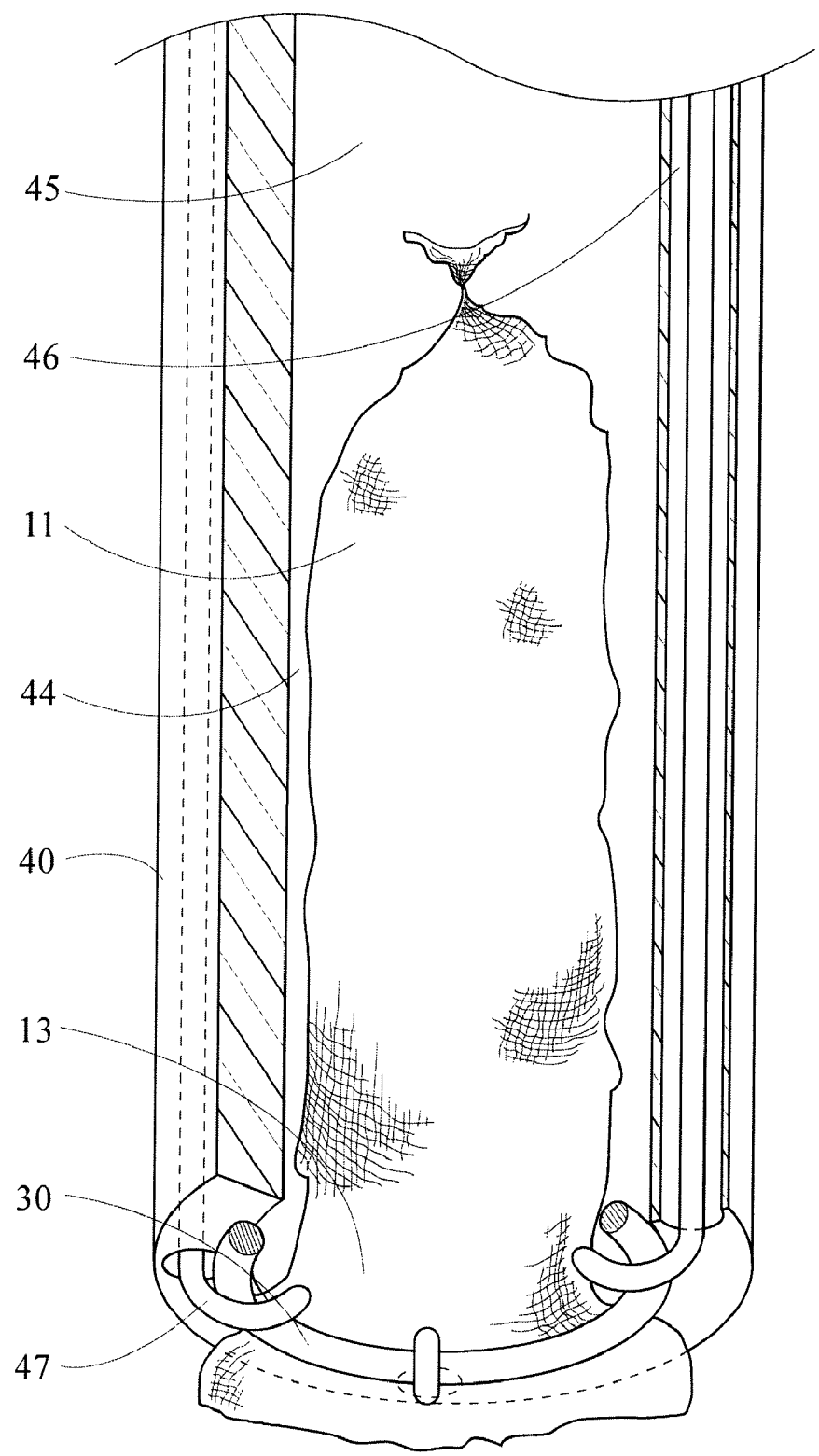
FIG. 13 is a cross-sectional view of FIG. 2.
Figure 14:
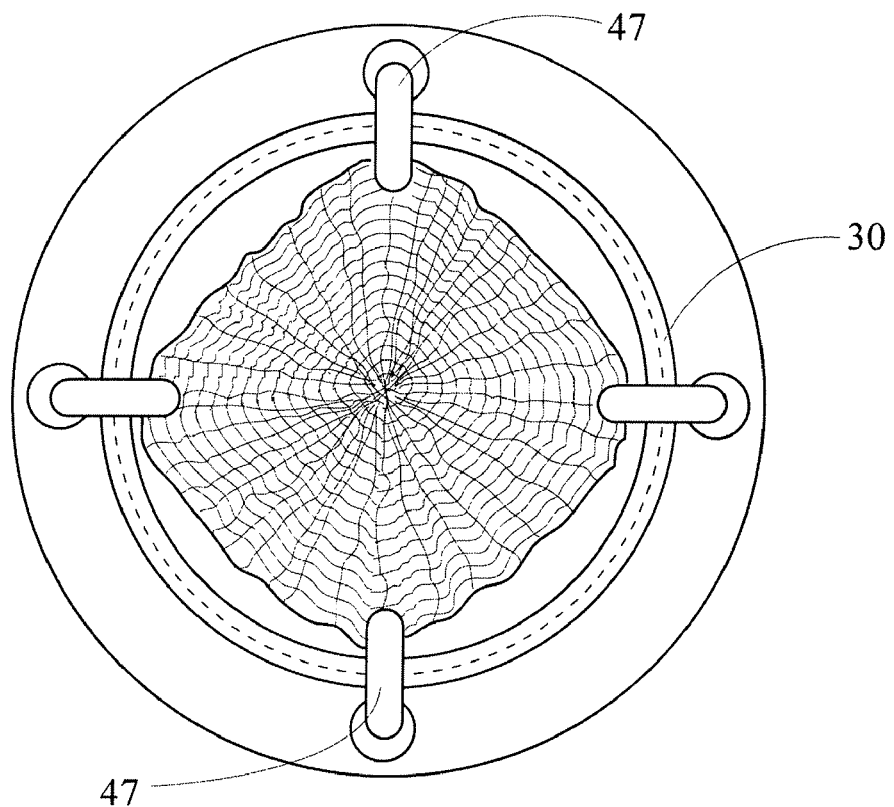
FIG. 14 is an end view of the distal end of the delivery tube in which a plurality of hooks are secured to the proximal end of the intragastric bag.

Having described the various components of the delivery system, a method of deploying the intragrastric bag 11 with the delivery system will now be discussed. First, the intragastric bag 11 is loaded into the main lumen 46 of the overtube 40, as shown in FIGS. 2 and 13, by the following procedure. The hooks 47 are configured such that a distal portion of each of the hooks 47 emerges from the distal portion of their respective lumens 46 to form a curved distal end (FIGS. 3 and 13). The proximal end 13 of the intragastric bag 11 is anchored onto the curved hooks 47 at the distal end 44 of the overtube 40, as shown in FIGS. 2 and 13. The distal end of the bag 11 is shown disposed within the lumen 45 of the overtube 40 (FIGS. 1 and 13). Referring to FIG. 2, with the bag 11 anchored to the overtube 40, the intragastric bag 11 is loaded in a compressed first configuration 17 into the main lumen 45 of the overtube 40. Endoscopic looping device 30 is also attached to one of the smaller lumens 46 not occupied by a hook holder 47, as shown in FIG. 3. The looping device 30 is positioned about an outer surface of each of the hooks 47 (FIG. 14) so as to create sufficient rigidity of the looping device 30.

Having the intragastric bag 11 secured to the distal end of the overtube 40 and loaded in a compressed first configuration 17 (FIG. 2) along the distal end 44 of the overtube 40, the overtube 40 is positioned within the patient such that the distal end 44 of the overtube 40 having the bag 11 attached thereto is positioned at the target site within the gastric lumen, as shown in FIG. 7. After positioning of the overtube 40, a pusher rod 1100 (FIGS. 11a, 11b) may be used to manually push the distal end 14 of the bag 11 until the distal end 14 is completely delivered into the gastric lumen, as shown in FIG. 7.

Figure 5:
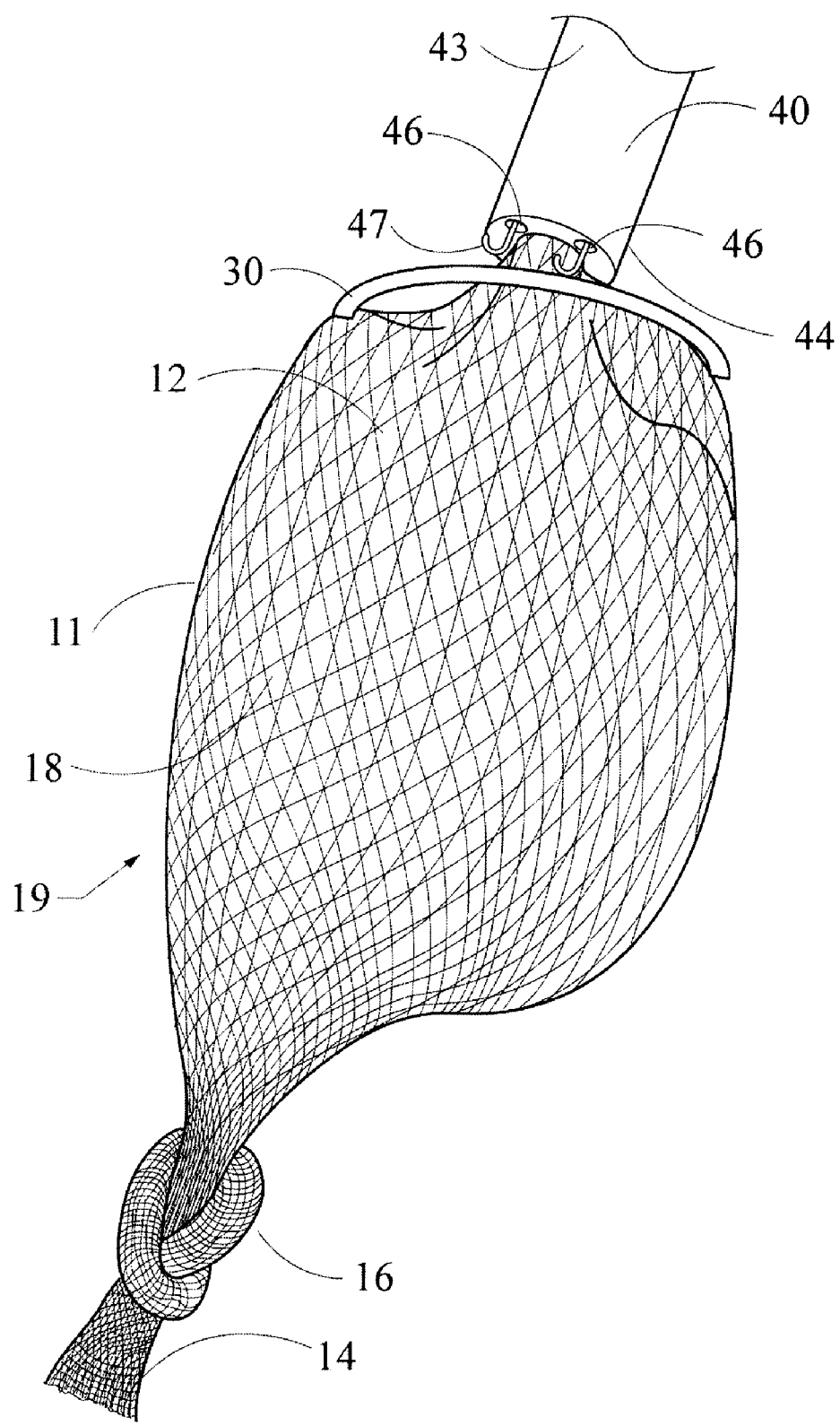
FIG. 5 depicts a pictorial view of the intragastric bag of FIG. 2 during delivery from the delivery tube into the gastric lumen.

Pushing the bag 11 into the gastric lumen causes the bag 11 to assume a second expanded configuration, as shown in FIG. 7. FIGS. 5 and 15 show the second expanded configuration of the bag 11 within the gastric lumen in greater detail. Specifically, FIGS. 5 and 13 show that the proximal end 13 of the bag 11 remains secured to the distal end 44 of the overtube 40 by anchoring to the retractable hooks 47. The endoscopic loop 30 circumferentially encloses the proximal end 13 of the bag 11 but does not close it so that the filler strip 100 may be inserted through the open proximal end 13 of the bag 11. The proximal portion of the endoscopic loop 30 extends through the lumen 46 at the distal end 44 of the overtube 40 (FIGS. 3 and 15). The distal end 14 of the bag 11 is detached from the overtube 40, being completely disposed within the gastric lumen (FIGS. 3, 5, and 15) The distal stopper 16, which may be a knot as shown in FIG. 5, allows the distal end 14 of the bag 11 to be sealed, thus allowing subsequent insertion of the filler strip into the bag 11 without risk of the filler strip 100 falling out from the bag 11.

With the overtube 40 and bag 11 positioned within the target site of the gastric lumen as shown in FIGS. 5, 7, and 15, the filler strip 100 of FIG. 8 may now be inserted into the bag 11. FIG. 12 shows that the filler strip 100 is inserted into the main lumen 45 of the overtube 40. The pusher rod 1100 (FIGS. 11a, 11b) is thereafter inserted into the main lumen 45 to push the filler strip 100 distally along the main lumen 45. Specifically, referring to FIG. 12, the flaps 1110 (FIGS. 11a and 11b) of the pusher rod 1100 engage, and may partially cut into the filler strip 100 material adjacent to the knots 116 and catch on the knots 16, thereby allowing the pusher rod 1100 to create sufficient force against the filler strip 100. The knots 116 are formed along the filler strip 100 (FIG. 8) to help the flaps 1110 of the pusher rod 100 distally push (as indicated by the arrow) sections between adjacent knots 116 of the filler strip 100. This sufficient force of the pusher rod 1100 against the knots 116 helps to push the filler strip 100 distally along the main lumen 45 of the overtube 40.

Eventually, the filler strip 100 will have reached the distal end 44 of the overtube 40. At this juncture, further pushing of the pusher rod 1100 against the filler strip 100 causes the filler strip 100 to be inserted into the main body 15 of the intragastric bag 11 located within the gastric lumen, as shown in FIG. 9. After the filler strip 100 has been inserted within bag 11, the pusher rod 1100 may be withdrawn through the main lumen 45 of the overtube 40.

With the filler strip 100 entirely within the bag 11, the proximal end 13 of the bag 11 may now be closed using endoscopic loop 30. Because the loop 30 is configured about the hooks 47, the loop 30 possesses sufficient rigidity to be tightened around the bag 11. The endoscopic loop 30 is tightened around the proximal end 13 of the bag 11 to close off the bag 11, as shown in FIG. 6 (filler strip 100 material not shown inside of bag 11). After the proximal end 13 of the bag 11 has been closed with endoscopic loop 30, a cutting device, such as forceps, may be inserted through the main lumen 45 of the overtube 40 to incise the endoscopic loop 30, thereby freeing the endoscopic loop 30 from the proximal end 13 of the bag 11. The incised loop 30 may be withdrawn with the forceps through the main lumen 45 of the overtube 40. Alternatively, the endoscopic loop may comprise the cable tie 1600 described in FIGS. 16 and 17. The cable tie 1600 has a weakened spot 1610 at which the proximal portion of the cable tie 1600 can break off from the distal portion of the cable tie 1600 (i.e., the portion enclosed about the bag 11), thereby eliminating the need to introduce a cutting device to cut the proximal portion.

Having closed the proximal end 13 of the bag 11, the overtube 40 may now be detached from the proximal end of the bag 11. Each of the hooks 47 are retracted proximally into their respective lumens 46, as shown in FIG. 6. As the hooks 47 move proximally into their respective lumens 46, they change from the curved configuration to the straightened configuration because of the compressive stress introduced into the hooks 47 by the walls of their respective lumens 46. As a result, each of the hooks 47 slip off from the proximal end 13 of the intragastric bag 11, thus completely releasing the proximal end of the bag 11 within the gastric lumen. FIG. 10 shows the resultant bag 10 with filler strip 100 contained therein within the gastric lumen. The overtube 40 has been withdrawn from the gastric lumen.

After a predetermined period of time, the bag 11 and filler strip 100 of FIG. 10 may be withdrawn from the gastric lumen. A cutting device may be introduced through the working channel of an endoscope to cut the endoscopic looping device 30 to loosen the proximal end 13 of the bag 11. After loosening the proximal end 13 of the bag 11, the filler strip 100 may be removed from the bag 11 with a retrieval device, such as forceps. Because the filler strip 100 has remained as a single strip, the filler strip may be removed from the bag 11 relatively quickly. After removal of the filler strip 100, the bag 11 may also be withdrawn from the gastric lumen with a retrieval device, such as forceps by using one hand to pull the endoscope while the other hand is used to grab the bag 11 with the forceps. Alternatively, the bag 11 and/or filler strip 100 may be formed from biodegradable materials such that they degrade within the gastric lumen over a predetermined period of time after weight loss has occurred. Accordingly, the biodegradable materials eliminate the need to withdraw the bag 11 and/or the filler strip 100 from the gastric lumen. Examples of possible biodegradable materials include polyethylene oxide (PEO), polydioxanone (PDS), polypropylene fumarate, poly(ethyl glutamate-co-glutamic acid), poly(tert-butyloxy-carbonylmethyl glutamate), polycaprolactones (PCL), polyhydroxybutyrates (PHBT), polyvalerolactones, polyhydroxyvalerates, poly(D,L-lactide-co-caprolactone) (PLA/PCL), polycaprolactone-glycolides (PGA/PCL), polyglycolic acids (PGA), polylactic acid (PLA), poly(phosphate ester), and poly(hydroxy butyrate), polydepsipeptides, maleic anhydride copolymers, polyphosphazenes, polyiminocarbonates, polyhydroxymethacrylates, polytrimethylcarbonates, cyanoacrylate, polycyanoacrylates, hydroxypropyl-methylcellulose, polysaccharides (such as hyaluronic acid, chitosan and regenerate cellulose), fibrin, casein, and proteins (such as gelatin and collagen), poly-e-decalactones, polylactonic acid, polyhydroxybutanoic acid, poly(1,4-dioxane-2,3-diones), poly(1,3-dioxane-2-ones), poly-p-dioxanones, poly-b-maleic acid, polycaprolactonebutylacrylates, multiblock polymers, polyether ester multiblock polymers, poly(DTE-co-DT-carbonate), poly(N-vinyl)pyrrolidone, polyvinylalcohols, polyesteramides, glycolated polyesters, polyphosphoesters, poly[p-carboxyphenoxy)propane], polyhydroxypentanoic acid, polyethyleneoxide-propyleneoxide, polyurethanes, polyether esters such as polyethyleneoxide, polyalkeneoxalates, lipids, carrageenanes, polyamino acids, synthetic polyamino acids, zein, polyhydroxyalkanoates, pectic acid, actinic acid, carboxymethylsulphate, albumin, hyaluronic acid, heparan sulphate, heparin, chondroitinesulphate, dextran, b-cyclodextrines, gummi arabicum, guar, collagen-N-hydroxysuccinimide, lipides, phospholipides, resilin, and modifications, copolymers, and/or mixtures.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention.

The invention claimed is:

1. A delivery system for introducing an obesity device into a gastric lumen, comprising:
    an overtube including a proximal end, a distal end, a centrally disposed main lumen and a plurality of secondary lumens circumferentially disposed about the main lumen;
    an intragastric bag removably disposed within the main lumen of the overtube and being eversible therefrom;
    an attachment mechanism removably attaching a proximal end of the intragastric bag to the distal end of the overtube prior to the bag being released into the gastric lumen, the attachment mechanism comprising a plurality of retractable hooks extending through the plurality of secondary lumens, the plurality of hooks being adapted to secure the proximal end of the of the intragastric bag against the distal end of the overtube;
    an elongate strip of filler material adapted to be advanced through the main lumen of the overtube and into the intragastric bag;
    an endoscopic looping device being operably connected to at least one of the plurality of hooks, wherein the hooks are extending through the plurality of secondary lumens, the endoscopic looping device adapted to close the proximal end of the intragastric bag prior to being released into the gastric lumen, the endoscopic looping device being adapted to retain the strip of filler material within the intragastric bag; and
    a pusher rod having a proximal end and a distal end, the pusher rod being adapted to be advanced through the main lumen of the overtube, the pusher rod adapted for pushing the intragastric bag out of the main lumen and into the gastric lumen, and the pusher rod further adapted for pushing a the strip of filler material through the main lumen and into the intragastric bag.

2. The delivery system according to claim 1, the pusher rod including flaps at the distal end.

3. The delivery system according to claim 1, each of the plurality of retractable hooks movable from a curved configuration to a straight configuration, the plurality of retractable hooks in the curved configuration adapted to secure the intragastric bag directly to the distal end of the overtube, and the plurality of retractable hooks in the straight configuration adapted to release the intragastric bag from the distal end of the overtube, wherein the plurality of retractable hooks are moved from the curved configuration to the straight configuration by retracting the retractable hooks into the secondary lumens of the overtube.

4. The delivery system according to claim 3, wherein the plurality of retractable hooks are formed from a shape memory alloy.

* * * * *

UNITED STATES PATENT AND TRADEMARK OFFICE
CERTIFICATE OF CORRECTION

| | | |
|---|---|---|
| PATENT NO. | : 8,007,507 B2 | |
| APPLICATION NO. | : 11/801442 | |
| DATED | : August 30, 2011 | |
| INVENTOR(S) | : David F. Waller | |

It is certified that error appears in the above-identified patent and that said Letters Patent is hereby corrected as shown below:

In the Claims

In column 10, claim 1, line 48, after "adapted for pushing" delete "a".

Signed and Sealed this
Eighteenth Day of October, 2011

David J. Kappos
*Director of the United States Patent and Trademark Office*